Figure 1:
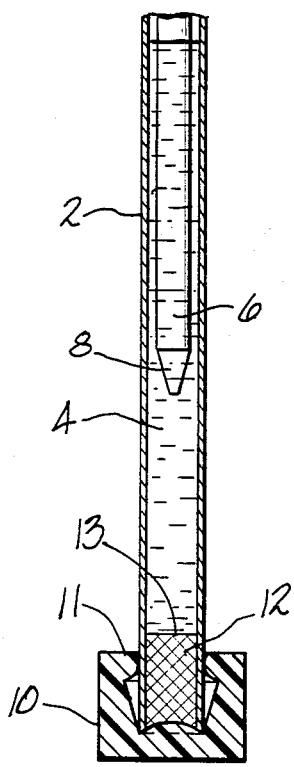

United States Patent [19]

Wardlaw et al.

[11] Patent Number: 4,567,754

[45] Date of Patent: Feb. 4, 1986

[54] MEASUREMENT OF SMALL HEAVY CONSTITUENT LAYER IN STRATIFIED MIXTURE

[76] Inventors: Stephen C. Wardlaw, 128 Sunset Hill Dr., Branford, Conn. 06405; Robert A. Levine, 31 Pilgrim La., Guilford, Conn. 06437

[21] Appl. No.: 717,361

[22] Filed: Mar. 29, 1985

[51] Int. Cl.⁴ .............................................. B01D 21/26
[52] U.S. Cl. ................... 73/61.1 R; 73/149; 73/61.4; 436/70; 422/55; 422/59
[58] Field of Search ................ 73/61.1 R, 149, 53, 73/64.1, 426; 128/637, 638, 771; 422/68, 55, 58, 59; 210/927, 787; 436/70, 63, 177; 494/10, 16

[56] References Cited

U.S. PATENT DOCUMENTS

| | | | |
|---|---|---|---|
| 3,508,653 | 4/1970 | Coleman | 128/771 |
| 3,852,194 | 12/1974 | Zine, Jr. | 494/16 |
| 3,914,985 | 10/1975 | Von Behrens | 73/61.4 X |
| 4,027,660 | 6/1977 | Wardlaw et al. | 73/149 X |
| 4,077,396 | 3/1978 | Wardlaw et al. | 73/149 X |
| 4,082,085 | 4/1978 | Wardlaw et al. | 73/61.1 R |
| 4,091,659 | 5/1978 | Massey et al. | 73/61.4 |
| 4,134,832 | 1/1979 | Heimreid | 436/177 |
| 4,137,755 | 2/1979 | Wardlaw et al. | 73/61.1 R |
| 4,180,465 | 12/1979 | Murty | 494/16 |

FOREIGN PATENT DOCUMENTS 195137  11/1983  Japan .................. 73/149

Primary Examiner—Stewart J. Levy
Assistant Examiner—Hezron E. Williams
Attorney, Agent, or Firm—William W. Jones

[57] ABSTRACT

A complex liquid, such as a biological liquid, is stratified, as by centrifugation in a tube, into constituent layers. The most dense or heaviest constituent layer is measured volumetrically by physically expanding the entire layer with a cylindrical float which is inserted in the tube and which occupies the portion of the tube also occupied by the constituent layer being measured. The axial extent of the expanded layer is measured to provide an indication of the volume of the layer being measured. The end of the tube proximate to the layer being measured contains a plug of a more dense material which is immiscible with the subject liquid and into which the float will settle during centrifugation. The float thus settles into the plug of dense material and "floats" therein so as to extend through the entirety of the layer being measured.

8 Claims, 2 Drawing Figures

U.S. Patent  Feb. 4, 1986  4,567,754

MEASUREMENT OF SMALL HEAVY CONSTITUENT LAYER IN STRATIFIED MIXTURE

This invention relates to the measurement of a dense constituent layer in a stratified multi-constituent liquid such as blood, or some other biological liquid.

We have invented a procedure for measuring the volume, or constituent count, of one or more constituents of a stratified liquid, such as blood, which procedure involves the use of a plastic float disposed in a centrifuged sample of the liquid. Specifically, our prior art procedure involves the use of a cylindrical plastic float which is disposed in a capillary tube into which a blood sample is drawn. An anticoagulant is comixed with the blood sample, and a stain such as acridine orange is also admixed with the blood sample. The anticoagulated sample, stain, and float are centrifuged in the capillary tube with the lower end of the tube being closed with a plastic cap made from polyethylene, or the like. Upon centrifugation, the float will settle into and float upon the red cell layer and extend through the white cell and platelet layers so as to physically elongate the white cell and platelet layers. The red cell layer is not significantly elongated by the float as the latter does not appreciably extend into the red cell layer. In a typical blood sample, the red cells are present in sufficient numbers to easily support the float to a degree that the float is not a factor in measuring the red cell count. The procedure does admit to red cell count measurement, but the effect of the float therein is not a determinative factor. The several facets of the procedure described above are disclosed in U.S. Pat. Nos. 4,027,660; 4,082,085; 4,077,396; and others.

It will be readily appreciated that the above-noted prior art procedure can provide a quick, accurate measurement for all of the constituents of the liquid, save the most dense thereof, in which the float must only partially extend so as to be buoyed thereby.

The present invention adapts the general procedure described above to enable volumetric or "count" measurement of the most dense, or heaviest, of the constituents when the amount thereof present in the sample is not sufficient to buoy the float. The prior art described above does not enable such a measurement to be made. The present invention can thus be used to accurately measure the red cell count in a plasmapheresis sample. After plasmapheresis, the material obtained cannot be used when the red cell count exceeds about one percent. Presently, an accurate red cell count cannot be measured in such samples below about five percent.

It will be appreciated that the prior art cell count procedures described above cannot be used to measure the red cell count in a plasmapheresis sample since the lower portions of the prior art floats are configured to float in the heaviest cell layer and, thus, are tapered at the bottom. Even if the floats are made with a perfectly flat bottom surface, sufficient red cells will become trapped between the bottom of the float and the plastic cap closure of the bottom of the tube to produce erroneous cell counts. In order to adapt the prior art cell count methodology referred to above to allow its use in the measurement of red cell counts in a plasmapheresis sample, we add a substance to the interior of the tube bottom inside of the plastic closure cap which is more dense than the most dense component of the sample, e.g., the red cells, and which is immiscible with the sample. The added substance may be present in an amount sufficient to buoy the float in the same manner that it would be buoyed in a normal blood sample. In any event, the added material must be present in a sufficient amount to completely fill the void between the plastic bottom closure cap and the bottom of the float so that the float will stick in the added material. At the same time, the added material elevates the red cell layer in the tube so that the float will extend through the entirety of the depleted red cell layer. The depleted red cell layer is thus expanded physically in the same way that a white cell layer is expanded by the float in the prior art described above. An example of a specific material which can be added to the tube in order to allow red cell measurement of a plasmapheresis sample is a relatively thixotropic mixture of kaolin and iodinated oil (Lipidol). This material is added to the bottom of the tube as a small pellet before the closure cap is put on the tube. The plasmapheresis sample is centrifuged with the float in the thusly closed tube. The added material will support the float sufficiently to prevent red cells from being trapped between the bottom of the float and the closure cap, and the entire red cell layer will be confined to the space between the exterior of the float and the interior of the tube. The measurement will be made with an instrument such as is disclosed in U.S. Pat. No. 4,156,570.

It is, therefore, an object of this invention to provide a procedure for quickly and accurately measuring the volume of a low volume heaviest or most dense layer in a stratified mixture contained in a transparent tube.

It is a further object of this invention to provide a procedure of the character described wherein a float is disposed in the tube along with an added material which is more dense than the layer being measured and immiscible with the mixture of the tube.

It is an additional object of this invention to provide a procedure of the character described wherein the float settles onto the layer of added material during a centrifugation step sufficiently to prevent any of the material in the layer being measured from being trapped between the lower end of the float and a plastic cap which closes the lower end of the tube during the centrifugation.

It is yet another object of this invention to provide a procedure of the character described wherein the layer being measured settles onto the layer of added material so that the float extends through the entirety of the layer being measured so as to physically elongate that layer to enable a measurement of its axial extent to be converted into a volumetric value for that layer.

Figure 2:
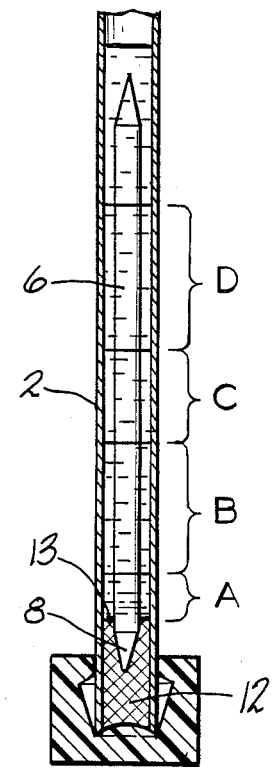

These and other objects of the invention will become more readily apparent from the following detailed disclosure of a preferred embodiment of the invention when taken in conjunction with the accompanying drawings in which:

FIG. 1 is a fragmented axial sectional view of a tube, such as a capillary tube, having a plug of dense material inserted in its lower end, a plastic cap closing its lower end, a material sample disposed therein, and a float disposed in the tube and the material sample; and FIG. 2 is a sectional view similar to FIG. 1 but showing the results of centrifugation of the sample.

In the drawings, there is shown a tube 2, which is preferably a transparent capillary tube. A material sample 4, which is to have one or more of its components measured after centrifugal stratification, is disposed in the bore of the tube 2. An elongated generally cylindrical plastic float 6 is disposed in the tube 2 in the material sample 4. The float 6 has a tapered lower end 8. The lower end of the tube 2 is closed by a plastic cap 10 fitted thereon. Inside of the lower end of the tube, there is disposed a plug 12 of a material which is heavier than the heaviest constituent of the sample and which is immiscible with the sample material. The plug 12 may be inserted into the tube 2 by dipping the end of the tube 2 into a reservoir of the plugging material. After the plug 12 is inserted into the tube 2, the cap 10 is affixed to the plugged end of the tube 2. The upper surface 13 of the plug 12 is disposed above the corresponding upper surface 11 of the cap 10 thereby ensuring that none of the lowest constituent layer will be deposited within the area of the cap 10. Thus, the entirety of the heaviest lower constituent layer will be visible for measurement through the tube 2.

In FIG. 2, the sample is shown after centrifugation. When the sample is centrifuged, the float 6 moves down toward the bottom of the tube 2 sufficiently to bury the pointed end 8 in the high density support material 12. The upper surface 13 of the support material layer forms an even meniscus around the float 6 during centrifugation so that an accurate measuring line will result. The centrifugation will result in a layering of the various constituents A, B, C and D in the annular zone between the float 6 and the bore of the tube 2. The most dense of the constituents will be A and the least dense will be D. It will be noted that the most dense constituent A is not present in sufficient volume to support the float 6 by itself. The fact that the float 6 is sufficiently buoyed by the support material 12 to cover the pointed end 8 of the float 6 allows the float 6 to extend through the entirety of the most dense constituent layer A, and the fact that the surface 13 of the support material 12 forms an even meniscus allows an accurate measurement to be made of the axial extent of the constituent layer A from the meniscus surface 13 to the interface between the layers A and B. As noted previously, a stain such as acridine orange will be added to the sample so that the different layers A, B, C and D will be differentially colored, preferably fluorescently. It will be appreciated that this technique not only allows the most dense constituent layer A to be measured, but it also allows the remaining layers B, C, and D to be accurately measured despite the fact that the most dense layer A is not present in sufficient quantity to buoy the float 6.

It will be readily appreciated that the above-described technique will allow measurement of the red cell layer, as well as the remaining constituent layers in a centrifuged plasmapheresis sample. The measurement is quick and accurate and is made with an optical instrument of the general type described in U.S. Pat. No. 4,156,570 to S. C. Wardlaw. The material added to support the float need merely be more dense than the most dense constituent of the sample being measured, be immiscible with the sample being measured, and provide a regular meniscus at its upper surface when centrifuged. The added support material may be a solid, semi-solid, or a liquid. Materials such as a carbohydrate gel of ficoll, a halogenated silicone, or a highly cohesive suspension of materials with a sufficiently high density such as polytetrafluoroethylene grease may be used as the added high density support material.

Since many changes and variations of the disclosed embodiment of the invention may be made without departing from the inventive concept, it is not intended to limit the invention otherwise than as required by the appended claims.

What is claimed is:

1. A method for measuring the volume of a relatively small quantity of the most dense constituent of a multiconstituent fluent material mixture, said method comprising the steps of:
   (a) admitting a quantity of the material mixture into a transparent capillary tube;
   (b) positioning in one end of the tube a plug of a material which is immiscible with the material mixture and more dense than the most dense constituent of the material mixture;
   (c) closing said one end of the tube with a sealing closure cap;
   (d) positioning an elongated float in the tube, said float being formed from a plastic material which will sink through the most dense constituent of the material mixture;
   (e) centrifuging the tube and its contents to cause layering of the several constituents of the material mixture and to cause said float to sink sufficiently into said material plug to be supported thereby, whereby said float extends through the entirety of at least the most dense constituent layer in the centrifuged mixture; and
   (f) measuring the axial extent of at least the most dense constituent layer in the tube.

2. A method for measuring the volume of a relatively small quantity of the most dense constituent of a multiconstituent fluent material mixture, said method comprising the steps of:
   (a) admitting a quantity of the material mixture into a transparent capillary tube;
   (b) providing a stain in the tube which will differentially color the various constituents of the material mixture;
   (c) filling one end of the tube with a plug of material which is immiscible with the material mixture and more dense than the most dense constituent of the material mixture;
   (d) closing said one end of the tube with a sealing closure cap;
   (e) positioning an elongated float in the tube;
   (f) centrifuging the tube and its contents to cause layering of the several constituents of the material mixture and to cause the float to sink through the layer of the most dense of the constituents of the material mixture and embed in said material plug sufficiently to be supported thereby, said float extending through the entirety of at least a plurality of the several constituent layers formed in the tube; and
   (g) measuring the axial extent of at least the most dense of the constituent layers in the tube.

3. The method of claim 2 wherein said plug is a high density material selected from a group consisting of: a relatively thixotropic mixture of kaolin and iodinated oil; a carbohydrate gel of ficoll; a halogenated silicone; and a polytetrafluoroethylene grease.

4. A method for measuring the red cell count in a plasmapheresis sample, said method comprising the steps of:
   (a) admitting a portion of the plasmapheresis sample into a transparent capillary tube;
   (b) filling one end of the tube with a plug of a material which is immiscible with the plasmapheresis sample and more dense than red cells in the plasmapheresis sample;

(c) positioning an axially elongated float in the tube;

(d) centrifuging the tube and its contents to cause the red cells in the sample to form a layer adjacent to the material plug and to cause the float to settle into the material plug and extend through the entirety of the red cell layer; and (e) measuring the axial extent of the red cell layer.

5. The method of claim 4 further comprising the step of closing said one end of the tube with a plastic sealing cap prior to the centrifugation step.

6. The method of claim 4 further comprising the step of providing a stain in the tube to differentially color the various cell types in the sample.

7. The method of claim 6 wherein the stain is acridine orange.

8. The method of claim 4 wherein the plug material is a relatively thixotropic mixture of kaolin and iodinated oil.

* * * * *